US009439419B2

(12) United States Patent
Yin et al.

(10) Patent No.: US 9,439,419 B2
(45) Date of Patent: Sep. 13, 2016

(54) COMPOSITIONS OF DIBROMOMALONAMIDE AND THEIR USE AS BIOCIDES

(71) Applicant: Dow Global Technologies Inc., Midland, MI (US)

(72) Inventors: Bei Yin, Phoenixville, PA (US); Freddie L. Singleton, Collegeville, PA (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/018,886

(22) Filed: Feb. 9, 2016

(65) Prior Publication Data

US 2016/0165884 A1    Jun. 16, 2016

Related U.S. Application Data

(62) Division of application No. 13/876,534, filed as application No. PCT/US2010/050880 on Sep. 30, 2010, now Pat. No. 9,288,983.

(60) Provisional application No. 61/246,189, filed on Sep. 28, 2009.

(51) Int. Cl.
| | |
|---|---|
| *A01N 37/18* | (2006.01) |
| *A01N 37/30* | (2006.01) |
| *A01N 33/18* | (2006.01) |
| *A01N 35/08* | (2006.01) |
| *A01N 37/34* | (2006.01) |
| *A01N 47/48* | (2006.01) |
| *A61K 8/42* | (2006.01) |
| *A61K 8/46* | (2006.01) |
| *A61Q 19/00* | (2006.01) |
| *C09D 5/14* | (2006.01) |
| *C11D 3/32* | (2006.01) |
| *C11D 3/34* | (2006.01) |
| *C11D 3/48* | (2006.01) |

(52) U.S. Cl.
CPC .............. *A01N 37/18* (2013.01); *A01N 33/18* (2013.01); *A01N 35/08* (2013.01); *A01N 37/30* (2013.01); *A01N 37/34* (2013.01); *A01N 47/48* (2013.01); *A61K 8/42* (2013.01); *A61K 8/46* (2013.01); *A61Q 19/00* (2013.01); *C09D 5/14* (2013.01); *C11D 3/32* (2013.01); *C11D 3/349* (2013.01); *C11D 3/48* (2013.01)

(58) Field of Classification Search
CPC .. A01N 37/30; A01N 2300/00; A01N 33/18; A01N 35/08; A01N 37/34; A01N 25/34; A01N 47/40; A01N 37/18; A01N 47/48; A61K 8/42; A61K 8/46; A61Q 19/00; C09D 5/14; C09D 3/32; C09D 3/349; C09D 3/48

See application file for complete search history.

(56) References Cited

U.S. PATENT DOCUMENTS

| | | | |
|---|---|---|---|
| 4,163,795 A | 8/1979 | Burk | |
| 4,725,587 A | 2/1988 | Whitekettle et al. | |
| 4,800,082 A | 1/1989 | Karbowski et al. | |
| 2004/0261196 A1 | 12/2004 | Ghosh et al. | |
| 2006/0231505 A1* | 10/2006 | Mayer | A01N 59/00 210/764 |
| 2010/0314318 A1 | 12/2010 | Gartner et al. | |

* cited by examiner

Primary Examiner — Sreeni Padmanabhan
Assistant Examiner — Jody Karol
(74) Attorney, Agent, or Firm — Tifani M. Edwards

(57) ABSTRACT

A biocidal composition comprising 2,2-dibromomalonamide and an electrophile containing biocide, and its use for the control of microorganisms in aqueous and water-containing systems.

6 Claims, No Drawings

COMPOSITIONS OF DIBROMOMALONAMIDE AND THEIR USE AS BIOCIDES

FIELD OF THE INVENTION

The invention relates to biocidal compositions and methods of their use for the control of microorganisms in aqueous and water-containing systems. The compositions comprise 2,2-dibromomalonamide and a biocidal compound containing at least one electrophilic moiety.

BACKGROUND OF THE INVENTION

Water systems provide fertile breeding grounds for algae, bacteria, viruses, and fungi some of which can be pathogenic. Microbial contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that yield one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and a biocidal compound containing at least one electrophilic moiety ("electrophile containing biocide"), wherein the electrophile containing biocide is selected from the group consisting of 2-bromo-2-nitropropane-1,3-diol, bromonitrostyrene, methylene bis(thiocyanate), and 1,2-dibromo-2,4-dicyanobutane.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and an electrophile containing biocide selected from the group consisting of 2-bromo-2-nitropropane-1,3-diol, bromonitrostyrene, methylene bis(thiocyanate), and 1,2-dibromo-2,4-dicyanobutane. It has surprisingly been discovered that combinations of 2,2-dibromomalonamide and an electrophile containing biocide as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

The term "2,2-dibromomalonamide" refers to a compound represented by the following chemical formula:

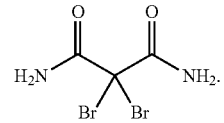

2,2-Dibromomalonamide and the electrophile containing biocides of the invention are commercially available and/or can be readily prepared by those skilled in the art using well known techniques.

In some embodiments of the invention, the weight ratio of 2,2-dibromomalonamide to the electrophile containing biocide is between about 100:1 and about 1:100.

In some embodiments, the weight ratio of 2,2-dibromomalonamide to the electrophile containing biocide is between about 40:1 and about 1:30.

In some embodiments, the weight ratio of 2,2-dibromomalonamide to the electrophile containing biocide is between about 32:1 and about 1:20.

In some embodiments, the electrophile containing biocide is 2-bromo-2-nitropropane-1,3-diol and the weight ratio of 2,2-dibromomalonamide to 2-bromo-2-nitropropane-1,3-diol is from about 100:1 to about 1:20, alternatively from about 70:1 to about 1:10, alternatively from about 40:1 to about 1:5, or alternatively from about 32:1 to about 1:2. In some embodiments, the weight ratio is about 9:1 to about 3:1.

In some embodiments, the electrophile containing biocide is bromonitrostyrene and the weight ratio of 2,2-dibromomalonamide to bromonitrostyrene is from about 100:1 to about 1:20, alternatively from about 70:1 to about 1:10, alternatively from about 40:1 to about 1:5, or alternatively from about 32:1 to about 1:2.

In some embodiments, the electrophile containing biocide is methylene bis(thiocyanate) and the weight ratio of 2,2- dibromomalonamide to methylene bis(thiocyanate) is from about 40:1 to about 1:10, alternatively from about 32:1 to about 1:1, or alternatively from about 32:1 to about 4:1.

In some embodiments, the electrophile containing biocide is 1,2-dibromo-2,4-dicyanobutane and the weight ratio of 2,2-dibromomalonamide to 1,2-dibromo-2,4-dicyanobutane is from about 20:1 to about 1:10, alternatively from about 10:1 to about 1:1, or alternatively from about 8:1 to about 2:1.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water), oilfield functional fluids such as drilling muds and fracturing fluids, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and electrophile containing biocide) is typically at least about 1 ppm, alternatively at least about 3 ppm, alternatively at least about 7 ppm, alternatively at least about 10 ppm, alternatively at least about 30 ppm, or alternatively at least about 100 ppm based on the total weight of the aqueous or water containing system. In some embodiments, a suitable upper limit for the actives concentration is about 1000 ppm, alternatively about 500 ppm, alternatively about 100 ppm, alternatively about 50 ppm, alternatively about 30 ppm, alternatively about 15 ppm, alternatively about 10 ppm, or alternatively about 7 ppm, based on the total weight of the aqueous or water containing system.

The components of the composition can be added to the aqueous or water containing system separately, or pre-blended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

The results provided in the Examples are generated using a growth inhibition assay or a kill assay. Details of each assay are provided below.

Kill Assay. This assay is used as a preliminary evaluation of synergy between the actives. The procedure is as follows. A mineral salts solution (0.2203 g of $CaCl_2$, 0.1847 g of $MgSO_4$, and 0.2033 g of $NaHCO_3$ in 1 L water, approximately pH 8) is inoculated with equal amounts (about 100 CFU/ml) of a mixture of *Pseudomonas aeruginosa* ATCC 10045 and *Staphylococcus aureus* ATCC 6538. Aliquots of the cell suspension are then treated with 2,2-dibromomalonamide ("DBMAL"), an electrophile containing biocide, and their combinations at various concentration levels. After incubating at 37° C. for 2 hours, the biocidal efficacy is determined on the basis of the minimum biocide concentration (MBC) needed to completely kill the bacterial cells in the aliquots. The MBC values are then used to calculate a synergy index (SI) values.

Summaries of the kill assay results are presented in the individual Examples. In each table, MBC values for each biocide and the blends tested are presented. Likewise, the Synergy Index ("SI") values for the combinations are listed. SI is calculated with the following equation:

$$\text{Synergy Index} = M_{DBMAL}/C_{DBMAL} + M_B/C_B$$

where $C_{DBMAL}$: Concentration of DBMAL required to inhibit bacterial growth when used alone $C_B$: Concentration of biocide (B) required to inhibit bacterial growth when used alone.

$M_{DBMAL}$: Concentration of DBMAL required to inhibit bacterial growth when used in combination with biocide (B).

$M_B$: Concentration of biocide (B) required to inhibit bacterial growth when used in combination with DBMAL The SI values are interpreted as follows:

SI<1: Synergistic combination

SI=1: Additive combination

SI>1: Antagonistic combination

Growth Inhibition Assay. The growth inhibition assay used in the Examples measures inhibition of growth (or lack thereof) of a microbial consortium Inhibition of growth can be the result of killing of the cells (so no growth occurs), killing of a significant portion of the populations of cells so that regrowth requires a prolonged time, or inhibition of growth without killing (stasis). Regardless of the mechanism of action, the impact of a biocide (or combination of biocides) can be measured over time on the basis of an increase in the size of the community.

The assay measures the efficacy of one or more biocides at preventing growth of a consortium of bacteria in a dilute mineral salts medium. The medium contains (in mg/l) the following components: $FeCl_3.6H_2O$ (1); $CaCl_2.2H_2O$ (10); $MgSO_4.7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 ul quantities to sterile microtiter plate wells. Dilutions of DBMAL and/or "Biocide B" are then added to the microtiter plate. After preparing the combinations of actives as illustrated below, each well is inoculated with 100 μl of a cell suspension containing ca. 1×100 cells per milliliter of a mixture of *Pseudomonas aeruginosa, Klebsiella pneumoniae, Staphylococcus aureus*, and *Bacillus subtilis*. The final total volume of medium in each well is 300 μl. Once prepared as described herein, the concentration of each active ranges from 25 ppm to 0.19 ppm as illustrated in Table 1. The resulting matrix allows testing of eight concentrations of each active and 64 combinations of actives in the ratios (of actives).

TABLE 1

Template for microtiter plate-based synergy assay showing concentrations of each active. Ratios are based on weight (ppm) of each active.

| | | | | | DBMAL (ppm) | | | | |
|---|---|---|---|---|---|---|---|---|---|
| | | 25.0 | 12.5 | 6.25 | 3.13 | 1.56 | 0.78 | 0.39 | 0.19 |
| Biocide | 25.0 | 1:1 | 1:2 | 1:4 | 1:8 | 1:16 | 1:32 | 1:64 | 1:128 |
| B (ppm) | 12.5 | 2:1 | 1 | 1:2 | 1:4 | 1:8 | 1:16 | 1:32 | 1:64 |
| | 6.25 | 4:1 | 2:1 | 1 | 1:2 | 1:4 | 1:8 | 1:16 | 1:32 |
| | 3.13 | 8:1 | 4:1 | 2:1 | 1 | 1:2 | 1:4 | 1:8 | 1:16 |
| | 1.56 | 16:1 | 8:1 | 4:1 | 2:1 | 1 | 1:2 | 1:4 | 1:8 |
| | 0.78 | 32:1 | 16:1 | 8:1 | 4:1 | 2:1 | 1 | 1:2 | 1:4 |
| | 0.39 | 64:1 | 32:1 | 16:1 | 8:1 | 4:1 | 2:1 | 1 | 1:2 |
| | 0.19 | 128:1 | 64:1 | 32:1 | 16:1 | 8:1 | 4:1 | 2:1 | 1:1 |

Controls (not shown) contain the medium with no biocide added. After preparing the combinations of actives as illustrated above, each well is inoculated with 100 µl of a cell suspension containing ca. 1×100 cells per milliliter of a mixture of *Pseudomonas aeruginosa, Klebsiella pneumoniae, Staphylococcus aureus*, and *Bacillus subtilis*. The final total volume of medium in each well is 300 µl.

Immediately after the microtiter plates are prepared, the optical density (OD) readings for each well is measured at 580 nm and the plates are then incubated at 37° C. for 24 hr. After the incubation period, the plates are gently agitated before $OD_{580}$ values are collected. The $OD_{580}$ values at $T_0$ are subtracted from $T_{24}$ values to determine the total amount of growth (or lack thereof) that occurs. These values are used to calculate the percent inhibition of growth caused by the presence of each biocide and each of the 64 combinations. A 90% inhibition of growth is used as a threshold for calculating synergy index (SI) values with the following equation:

Synergy Index=$M_{DBMAL}/C_{DBMAL}+M_B/C_B$ where
$C_{DBMAL}$: Concentration of DBMAL required to inhibit ~90% of bacterial growth when used alone
$C_B$: Concentration of biocide (B) required to inhibit ~90% of bacterial growth when used alone.
$M_{DBMAL}$: Concentration of DBMAL required to inhibit ~90% of bacterial growth when used in combination with biocide (B).
$M_B$: Concentration of biocide (B) required to inhibit ~90% of bacterial growth when used in combination with DBMAL The SI values are interpreted as follows:
SI<1: Synergistic combination
SI=1: Additive combination
SI>1: Antagonistic combination In the Examples below, the amounts of biocides in the solution are measured in mg per liter of solution (mg/l). Since solution densities are approximately 1.0, the mg/l measurement corresponds to weight ppm. Both units may therefore be used interchangeably in the Examples.

Example 1

DBMAL and Bronopol

Kill Assay Results. Table 2 summarizes the results for assays using DBMAL alone and in combination with 2-bromo-2-nitropropane-1,3-diol ("Bronopol" or "BNPD"). The results indicate synergy between the actives (Table 2).

TABLE 2

MBC of DBMAL, Bronopol, and combinations thereof.

| Active weight ratio (1st:2nd) | 1st biocide DBMAL | 2nd biocide Bronopol | Synergy Index |
|---|---|---|---|
| DBMAL alone | 66.7 | 0.0 | |
| 9:1 | 60.0 | 6.7 | <0.94 |
| 3:1 | 50.0 | 16.7 | <0.58 |
| 1:1 | 50.0 | 50.0 | <1.08 |
| 1:3 | 37.5 | 100.5 | <1.31 |
| 1:9 | >15 | >135 | NA |
| Bronopol alone | 0.0 | >150 | |

Inhibition Growth Assay Results. Table 3 shows the inhibition growth assay results for DBMAL, THPS, and combinations. In the assay, the minimum concentration of DBMAL in which growth of the consortium is at least 90% less than controls ($I_{90}$ value) is 12.5 mg/l. The $I_{90}$ value for Bronopol is 6.25 mg/ml.

TABLE 3

Percent inhibition of growth in a species-defined microbial consortium by Bronopol (BNPD) and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and BNPD | | | | | | | | |
|---|---|---|---|---|---|---|---|---|---|---|---|---|---|
| | DBMAL Concn. (mg/l) | % Inhibition of growth by DBMAL | BNPD Concn. (mg/l) | % Inhibition of growth by BNPD | DBMAL Concn. (mg/l) | BNPD Concn. (mg/l) | | | | | | | |
| | | | | | | 25.0 | 12.5 | 6.25 | 3.13 | 1.56 | 0.78 | 0.39 | 0.19 |
| 18 | 25.0 | 100 | 25.0 | 97 | 25.0 | 100 | 100 | 98 | 99 | 100 | 100 | 99 | 99 |
| 0 | 12.5 | 97 | 12.5 | 99 | 12.5 | 100 | 99 | 94 | 99 | 99 | 99 | 99 | 99 |
| 11 | 6.25 | 0 | 6.25 | 96 | 6.25 | 99 | 98 | 97 | 97 | 97 | 97 | 66 | 50 |

TABLE 3-continued

Percent inhibition of growth in a species-defined microbial consortium by Bronopol (BNPD) and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and BNPD | | | | | | | | |
|---|---|---|---|---|---|---|---|---|---|---|---|---|---|
| | DBMAL Concn. (mg/l) | % Inhibition of growth by DBMAL | BNPD Concn. (mg/l) | % Inhibition of growth by BNPD | DBMAL Concn. (mg/l) | BNPD Concn. (mg/l) | | | | | | | |
| | | | | | | 25.0 | 12.5 | 6.25 | 3.13 | 1.56 | 0.78 | 0.39 | 0.19 |
| 7 | 3.13 | 17 | 3.13 | 67 | 3.13 | 92 | 98 | 95 | 98 | 91 | 0 | 0 | 0 |
| 7 | 1.56 | 13 | 1.56 | 0 | 1.56 | 99 | 100 | 99 | 99 | 19 | 0 | 0 | 0 |
| 5 | 0.78 | 12 | 0.78 | 0 | 0.78 | 99 | 99 | 96 | 98 | 0 | 0 | 0 | 0 |
| 7 | 0.39 | 8 | 0.39 | 0 | 0.39 | 99 | 92 | 92 | 97 | 0 | 0 | 0 | 0 |
| 2 | 0.19 | 4 | 0.19 | 0 | 0.19 | 99 | 99 | 96 | 97 | 0 | 0 | 0 | 0 |

Table 4 shows ratios of DBMAL and bronopol (BNPD) found to be synergistic under the growth inhibition assay.

TABLE 4

| DBMAL Concn. (mg/l) | BNPD Concn. (mg/l) | Ratio (DBMAL to BNPD) | Synergy Index (SI) |
|---|---|---|---|
| 6.25 | 0.19 | 32:1 | 0.53 |
| 6.25 | 0.39 | 16:1 | 0.56 |
| 3.13 | 0.19 | 16:1 | 0.28 |
| 6.25 | 0.78 | 8:1 | 0.64 |
| 3.13 | 0.39 | 8:1 | 0.31 |
| 6.25 | 1.56 | 4:1 | 0.75 |
| 3.13 | 0.78 | 4:1 | 0.38 |
| 3.13 | 1.56 | 2:1 | 0.5 |
| 3.13 | 3.13 | 1:1 | 0.75 |
| 1.56 | 3.13 | 1:2 | 0.63 |

Example 2

DBMAL and BNS

Inhibition Growth Assay Results. Table 5 shows the inhibition growth assay results for DBMAL, bromonitrostyrene ("BNS"), and combinations thereof. The $I_{90}$ values for DBMAL and BNS are 12.5 mg/l and 6.25 mg/l, respectively.

Table 6 shows concentrations of DBMAL and BNS found to be synergistic under the growth inhibition assay. Ratios are based on concentrations of actives.

TABLE 6

| DBMAL Concn. (mg/l) | BNS Concn. (mg/l) | Ratio (DBMAL to BNS) | Synergy Index (SI) |
|---|---|---|---|
| 6.25 | 0.19 | 32:1 | 0.53 |
| 6.25 | 0.39 | 16:1 | 0.56 |
| 6.25 | 0.78 | 8:1 | 0.63 |
| 6.25 | 1.56 | 4:1 | 0.75 |
| 3.13 | 1.56 | 2:1 | 0.5 |
| 3.13 | 3.13 | 1:1 | 0.75 |
| 1.56 | 3.13 | 1:2 | 0.63 |

Example 3

DBMAL and MBT

Inhibition Growth Assay Results. Table 7 shows the inhibition growth assay results for DBMAL, methylene bis(thiocyanate) ("MBT"), and combinations. The $I_{90}$ values for DBMAL and MBT are 12.5 mg/l and 0.78 mg/l, respectively.

TABLE 5

Percent inhibition of growth in a species-defined microbial consortium by BNS and DBMAL alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and BNS | | | | | | | | |
|---|---|---|---|---|---|---|---|---|---|---|---|---|---|
| | DBMAL Concn. (mg/l) | % Inhibition of growth by DBMAL | BNS Concn. (mg/l) | % Inhibition of growth by BNS | DBMAL Concn. (mg/l) | BNS Concn. (mg/l) | | | | | | | |
| | | | | | | 25.0 | 12.5 | 6.25 | 3.13 | 1.56 | 0.78 | 0.39 | 0.19 |
| 49 | 25.0 | 98 | 25.0 | 99 | 25.0 | 98 | 100 | 100 | 100 | 100 | 100 | 100 | 99 |
| 0 | 12.5 | 98 | 12.5 | 100 | 12.5 | 100 | 100 | 100 | 100 | 100 | 100 | 97 | 96 |
| 1 | 6.25 | 65 | 6.25 | 100 | 6.25 | 100 | 100 | 100 | 100 | 100 | 100 | 100 | 97 |
| 4 | 3.13 | 34 | 3.13 | 75 | 3.13 | 84 | 100 | 100 | 100 | 100 | 0 | 0 | 0 |
| 0 | 1.56 | 11 | 1.56 | 42 | 1.56 | 100 | 100 | 100 | 100 | 23 | 4 | 0 | 0 |
| 0 | 0.78 | 6 | 0.78 | 19 | 0.78 | 100 | 100 | 100 | 50 | 13 | 5 | 0 | 0 |
| 0 | 0.39 | 1 | 0.39 | 0 | 0.39 | 100 | 100 | 100 | 50 | 16 | 0 | 0 | 0 |
| 0 | 0.19 | 10 | 0.19 | 11 | 0.19 | 100 | 100 | 100 | 38 | 16 | 5 | 0 | 0 |

TABLE 7

Percent inhibition of growth in a species-defined microbial consortium by DBMAL and MBT alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and MBT | | | | | | | | |
|---|---|---|---|---|---|---|---|---|---|---|---|---|---|
| | DBMAL Concn. (mg/l) | % Inhibition of growth by DBMAL | MBT Concn. (mg/l) | % Inhibition of growth by MBT | DBMAL Concn. (mg/l) | MBT Concn. (mg/l) | | | | | | | |
| | | | | | | 25.0 | 12.5 | 6.25 | 3.13 | 1.56 | 0.78 | 0.39 | 0.19 |
| 20 | 25.0 | 98 | 25.0 | 94 | 25.0 | 98 | 98 | 95 | 94 | 98 | 96 | 98 | 97 |
| 0 | 12.5 | 100 | 12.5 | 95 | 12.5 | 98 | 96 | 96 | 98 | 99 | 98 | 98 | 95 |
| 0 | 6.25 | 41 | 6.25 | 97 | 6.25 | 98 | 100 | 100 | 100 | 100 | 100 | 100 | 100 |
| 29 | 3.13 | 61 | 3.13 | 100 | 3.13 | 98 | 100 | 100 | 10 | 100 | 100 | 100 | 63 |
| 20 | 1.56 | 52 | 1.56 | 100 | 1.56 | 99 | 100 | 100 | 100 | 100 | 100 | 57 | 39 |
| 33 | 0.78 | 58 | 0.78 | 98 | 0.78 | 98 | 100 | 100 | 100 | 100 | 100 | 32 | 0 |
| 0 | 0.39 | 23 | 0.39 | 24 | 0.39 | 98 | 99 | 100 | 100 | 100 | 46 | 0 | 0 |
| 36 | 0.19 | 25 | 0.19 | 22 | 0.19 | 99 | 98 | 82 | 98 | 98 | 1 | 0 | 0 |

Table 8 shows concentrations of DBMAL and MBT found to be synergistic. The ratios are based on concentrations of the actives.

TABLE 8

| DBMAL Concn. (mg/l) | MBT Concn. (mg/l) | Ratio (DBMAL:MBT) | Synergy Index (SI) |
|---|---|---|---|
| 6.25 | 0.19 | 32:1 | 0.75 |
| 3.13 | 0.19 | 16:1 | 0.5 |
| 3.13 | 0.39 | 8:1 | 0.75 |
| 1.56 | 0.19 | 8:1 | 0.38 |
| 1.56 | 0.39 | 4:1 | 0.63 |

Example 4

DBMAL and DBDCB

Inhibition Growth Assay Results. Table 9 shows the inhibition growth assay results for DBMAL, 1,2-Dibromo-2,4-dicyanobutane ("DBDCB"), and combinations thereof. The $I_{90}$ values for DBMAL and DBDCB are 6.25 mg/l.

Table 10 shows concentrations of DBMAL and DBDCB found to be synergistic.

TABLE 10

| DBMAL Concn. (mg/l) | DBDCB Concn. (mg/l) | Ratio (DBMAL to DBDCB) | Synergy Index (SI) |
|---|---|---|---|
| 3.13 | 1.56 | 2:1 | 0.75 |
| 3.13 | 0.78 | 4:1 | 0.63 |
| 3.13 | 0.39 | 8:1 | 0.56 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

TABLE 9

Percent inhibition of growth in a species-defined microbial consortium by DBMAL and DBDCB alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and DBDCB | | | | | | | | |
|---|---|---|---|---|---|---|---|---|---|---|---|---|---|
| | DBMAL Concn. (mg/l) | % Inhibition of growth by DBMAL | DBDCB Concn. (mg/l) | % Inhibition of growth by DBDCB | DBMAL Concn. (mg/l) | DBDCB Concn. (mg/l) | | | | | | | |
| | | | | | | 25.0 | 12.5 | 6.25 | 3.13 | 1.56 | 0.78 | 0.39 | 0.19 |
| 17 | 25.0 | 100 | 25.0 | 97 | 25.0 | 100 | 100 | 100 | 100 | 99 | 100 | 100 | 100 |
| 0 | 12.5 | 100 | 12.5 | 99 | 12.5 | 100 | 100 | 100 | 100 | 100 | 100 | 100 | 100 |
| 12 | 6.25 | 100 | 6.25 | 100 | 6.25 | 100 | 100 | 100 | 100 | 100 | 100 | 95 | 48 |
| 0 | 3.13 | 20 | 3.13 | 43 | 3.13 | 100 | 100 | 100 | 100 | 7 | 1 | 0 | 0 |
| 0 | 1.56 | 14 | 1.56 | 17 | 1.56 | 100 | 100 | 100 | 83 | 0 | 0 | 0 | 0 |
| 0 | 0.78 | 11 | 0.78 | 0 | 0.78 | 100 | 100 | 68 | 100 | 10 | 0 | 0 | 0 |
| 0 | 0.39 | 0 | 0.39 | 0 | 0.39 | 100 | 100 | 100 | 100 | 10 | 0 | 0 | 0 |
| 0 | 0.19 | 0 | 0.19 | 0 | 0.19 | 100 | 100 | 100 | 20 | 12 | 19 | 3 | 14 |

What is claimed is:

1. A synergistic biocidal composition for controlling microorganisms in an aqueous or water-containing system, the composition comprising 2,2-dibromomalonamide and bromonitrostyrene, wherein the weight ratio of 2,2-dibromomalonamide to bromonitrostyrene is from 32:1 to 1:2.

2. The synergistic composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration systems, swimming pool or spa water.

3. A method for controlling microorganism growth in an aqueous or water-containing system, the method comprising treating the aqueous or water-containing system with an effective amount of a composition according to claim 1.

4. A method according to claim 3 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration system, swimming pool or spa water.

5. A method according to claim 3 wherein the composition inhibits the growth of microorganisms in the aqueous or water-containing system.

6. A method according to claim 3 wherein the composition kills microorganisms in the aqueous or water-containing system.

* * * * *